US012539377B2

(12) United States Patent
Säll

(10) Patent No.: US 12,539,377 B2

(45) Date of Patent: Feb. 3, 2026

(54) AEROSOL ASSEMBLY FOR A MEDICAMENT DELIVERY DEVICE

(71) Applicant: SHL MEDICAL AG, Zug (CH)

(72) Inventor: Daniel Säll, Segeltorp (SE)

(73) Assignee: SHL MEDICAL AG, Zug (CH)

( * ) Notice: Subject to any disclaimer, the term of this patent is extended or adjusted under 35 U.S.C. 154(b) by 808 days.

(21) Appl. No.: 17/796,912

(22) PCT Filed: Nov. 27, 2020

(86) PCT No.: PCT/EP2020/083738

§ 371 (c)(1),
(2) Date: Aug. 2, 2022

(87) PCT Pub. No.: WO2021/160308

PCT Pub. Date: Aug. 19, 2021

(65) Prior Publication Data

US 2023/0057751 A1 Feb. 23, 2023

(30) Foreign Application Priority Data

Feb. 13, 2020 (EP) .................................... 20157044

(51) Int. Cl.
*A61M 15/00* (2006.01)

(52) U.S. Cl.
CPC ...... *A61M 15/009* (2013.01); *A61M 15/0026* (2014.02)

(58) Field of Classification Search
CPC ........................ A61M 15/009; A61M 15/0026; A61M 11/00; A61M 11/005; A61M 11/007;

(Continued)

(56) References Cited

U.S. PATENT DOCUMENTS 7,837,235 B2 11/2010 Geser et al.
2004/0159679 A1* 8/2004 Greiner-Perth ......... B05B 11/02 222/153.13

(Continued)

FOREIGN PATENT DOCUMENTS

EP 1706210 B1 12/2007
EP 2275160 A1 1/2011

(Continued)

OTHER PUBLICATIONS

International Search Report and Written Opinion for Int. App. No. PCT/EP2020/083738, mailed Feb. 18, 2021.

*Primary Examiner* — Victoria Murphy
*Assistant Examiner* — Tina Zhang
(74) *Attorney, Agent, or Firm* — McDonnell Boehnen Hulbert & Berghoff LLP

(57) ABSTRACT

An aerosol assembly for a medicament delivery device is provided having a nozzle chip assembly including a carrier and a nozzle chip provided on the carrier, a holding structure having a fluid channel extending through the holding structure, wherein the nozzle chip assembly is configured to be mounted into the fluid channel such that fluid flowing through the fluid channel passes through the nozzle chip, and an elastic sealing member configured to be arranged with a tight fit in the fluid channel, the sealing member having a central through-opening configured to receive the nozzle chip to seal the nozzle chip towards the carrier.

12 Claims, 5 Drawing Sheets

(58) Field of Classification Search
CPC ............ A61M 15/0065; A61M 11/003; A61M 2207/00; A61M 15/0021; A61M 15/0085; B05B 11/0032; B05B 11/1091; B05B 1/14; B05B 1/00; B05B 15/18; B05B 17/0646; C25D 7/00; C25D 1/08; C25D 3/567
USPC .......... 239/102.2, 102.1, 4, 596; 128/200.14, 128/200.23, 200.21
See application file for complete search history.

(56) References Cited

U.S. PATENT DOCUMENTS

| | | | | |
|---|---|---|---|---|
| 2008/0087688 | A1 * | 4/2008 | Twyman | A61M 15/009 222/402.2 |
| 2013/0199521 | A1 * | 8/2013 | Hausmann | A61M 11/007 128/200.23 |
| 2013/0345587 | A1 * | 12/2013 | Colman | A61M 39/10 600/532 |
| 2020/0368455 | A1 * | 11/2020 | Hua | B05B 17/0646 |
| 2020/0368468 | A1 * | 11/2020 | Liu | A61M 16/0066 |
| 2021/0387209 | A1 * | 12/2021 | Van Rijn | B05B 1/323 |

FOREIGN PATENT DOCUMENTS

| | | | |
|---|---|---|---|
| WO | 97/12683 | A1 | 4/1997 |
| WO | 03/097139 | A1 | 11/2003 |
| WO | 2012/007315 | A1 | 1/2012 |
| WO | 2015/194962 | A1 | 12/2015 |

* cited by examiner

AEROSOL ASSEMBLY FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2020/083738 filed Nov. 27, 2020, which claims priority to European Patent Application No. 20157044.7 filed Feb. 13, 2020.

TECHNICAL FIELD

The present disclosure generally relates to aerosol assemblies for medicament delivery devices.

BACKGROUND

Medicament delivery devices may be provided with a micro nozzle to create an aerosol of the therein contained medicament for example for inhalation. The nozzle is subjected to high pressure during medicament administration.

U.S. Pat. No. 7,837,235 B2 discloses a device for clamping a fluidic component. The fluidic component is arranged in an elastomeric shaped part, the contour of which is matched to the outer contour of the component and to the inner contour of a holder. The elastomeric part is chamfered towards the fluidic component on its pressure side. When the holder is assembled the elastomeric shaped part is deformed by a projection provided on the mating part and is put under uniformly distributed internal tension, after the elastomeric shaped parts surrounds the fluidic component to its full height. This "floating mounting" means that there are no unacceptable local tension peaks and no deformation of the component. The mounting is sealed against the fluid even when the fluid pressure fluctuates repeatedly from a very low level to several 100 bar.

SUMMARY

It is in general desirable to get rid of all air in a pressurised medicament delivery device during priming as trapped air will cause "drooling" on top of the nozzle after dosing. The drooling may create a crust on the nozzle when it dries, which may cause clogging.

An object of the present disclosure is to provide an aerosol assembly which solves, or at least mitigates problems of the prior art.

There is hence according to a first aspect of the present disclosure provided an aerosol assembly for a medicament delivery device, the aerosol assembly comprising: a nozzle chip assembly including a carrier and a nozzle chip provided on the carrier, a holding structure having a fluid channel extending through the holding structure, wherein the nozzle chip assembly is configured to be mounted into the fluid channel such that fluid flowing through the fluid channel passes through the nozzle chip, and an elastic sealing member configured to be arranged with a tight fit in the fluid channel, the sealing member having a central through-opening configured to receive the nozzle chip to seal the nozzle chip towards the carrier.

The elastic sealing member seals the nozzle chip towards the carrier, whereby the amount of air trapped around the nozzle chip is minimised. "Drooling" may thereby be reduced, and thus the risk of crust building up on the nozzle chip causing clogging is also reduced.

The nozzle chip is preferably a micro nozzle.

The nozzle chip may for example be glued onto the carrier.

The sealing member may bear against the inner surface of the fluid channel to obtain the tight fit with the fluid channel. The sealing member may hence be in direct contact with the inner surface of the fluid channel.

According to one embodiment the fluid channel has an inner surface provided with a circumferentially extending opening, wherein the carrier has an outer boundary portion mounted into the opening to hold the carrier in place. The carrier and hence the nozzle chip can thereby be held in place axially relative to the holding structure.

The opening may for example be in the form of a circumferentially extending slit configured to receive the outer boundary portion of the carrier. The carrier may be a planar substrate.

Luer lock interfaces are commonly used in medicament delivery devices. One drawback with Luer locks is that the thread is not self-locking. It is intended to be easily unscrewed to change e.g. a needle tip on a syringe. It has been found that there is a high risk that the Luer lock will come loose and leak after storage. The applicant has made tests that involved storage of a medicament delivery device with a Luer lock connection at an elevated temperature of 55° C. for 48 hours. It was found that the Luer lock threads unscrewed themselves during this time.

Another issue is that at high pressures, there is a risk that the Luer threads unscrew due to the force from the pressure. The applicant carried out a test with a male Luer lock member made of polypropylene (PP) and female Luer lock member made of PP and one made of polyethylene (PE). The female PP Luer lock member started to leak/come loose at 50 bar and the female PE Luer lock member started to leak/come loose at 20 bar. One way to overcome this problem is to alter the pitch. However, such modification is not always feasible as for example the threads will be small and difficult to mould/assemble with high yield.

On the positive side, an advantage with Luer lock connections is that they are easy to manufacture and give a strong and self-aligning interface. From this perspective, it is hence advantageous to use Luer lock connections. It would however be desirable to use Luer lock connections without the aforementioned drawbacks.

Therefore, one embodiment comprises a base member having a Luer cone configured to extend into the fluid channel towards the nozzle chip assembly, the Luer cone having a central channel extending through the base member and configured to extend coaxially with the fluid channel, wherein the base member and the holding structure have Luer threads by which the base member and the holding structure are configured to be connected, wherein the central through-opening of the sealing member is configured to open towards the central channel, and wherein the sealing member is configured to be arranged axially between the Luer cone and the carrier.

Thus, instead of using the Luer cone for sealing, the nozzle chip is sealed by means of the elastic sealing member. At the same time, the Luer connection provides a strong and self-aligning interface.

According to one embodiment the sealing member is configured to be in contact with the Luer cone and with the carrier. This contact may be a direct contact.

According to one embodiment the sealing member comprises a viscoelastic material.

According to one embodiment the viscoelastic material is an elastomer.

According to one embodiment the sealing member is rotationally symmetric.

According to one embodiment the central through-opening has a constant inner diameter along its entire extension.

The sealing member may have a first end surface which faces the carrier, wherein the first end surface is provided with a first groove that extends in the circumferential direction around the central through-opening of the sealing member. The first groove may hence function as a liquid collector in which dissipating liquid may accumulate, preventing any liquid that has started to dissipate in between the carrier and the first end surface to dissipate further.

The first end surface may bear against the carrier.

The sealing member may have a second end surface arranged at an opposite end of the sealing member relative to the first end surface, wherein the second end surface is provided with a second groove that extends in the circumferential direction around the central through-opening of the sealing member.

The second end surface may bear against an end face of the Luer cone. The second groove may hence function as a liquid collector in which dissipating liquid may accumulate, preventing any liquid that has started to dissipate in between the second end surface and the end face of the Luer cone to dissipate further.

According to one embodiment the sealing member is configured to be mounted in the fluid channel with a mounting compression of between 0.2 to 0.6 mm. This means that the sealing member is compressed between 0.2 and 0.6 mm when arranged in the fluid channel. In particular, the outer surface of the sealing member is compressed in this manner. The tight fit with the inner surface of the fluid channel is thereby achieved.

According to one embodiment the sealing member has an external surface provided with a rib extending in a circumferential direction of the sealing member. The rib is elastic and deformed when the sealing member is arranged in the fluid channel. The rib further reduces the risk of liquid flow between the sealing member and the inner surface of the fluid channel.

According to one embodiment the holding structure has a hollow generally cylindrical end portion in which the fluid channel extends axially, wherein the cylindrical end portion has an external surface provided with first Luer threads, and wherein the base member has an outer wall arranged concentrically with the Luer cone, wherein the cylindrical end portion is configured to be arranged concentrically between the Luer cone and the outer wall, the outer wall having second Luer threads configured to engage with the first Luer threads.

As an alternative to the aforementioned Luer lock solution, the base member and the holding structure may be configured to interlock with each other by means of a snap-fit mechanism.

By means of the sealing member the snap-fit mechanism will be able to withstand high pressure and the holding member will therefore not disengage from the base member, which would otherwise be a risk.

The base member may be provided with a plurality of gripping arms and the holding structure may be provided with radial protrusions, wherein each gripping arm is configured to engage with a respective radial protrusion, the gripping arms and the radial protrusions forming the snap-fit mechanism.

The gripping arms may be configured to extend parallel with the central longitudinal axis of the aerosol assembly.

The gripping arms may be configured to flex radially.

There is according to a second aspect of the present disclosure provided a medicament delivery device comprising an aerosol assembly according to the first aspect.

According to one embodiment the medicament delivery device is an inhaler.

Generally, all terms used in the claims are to be interpreted according to their ordinary meaning in the technical field, unless explicitly defined otherwise herein. All references to "a/an/the element, apparatus, component, means, etc." are to be interpreted openly as referring to at least one instance of the element, apparatus, component, means, etc., unless explicitly stated otherwise.

BRIEF DESCRIPTION OF THE DRAWINGS

The specific embodiments of the present disclosure will now be described, by way of example, with reference to the accompanying drawings, in which.

DETAILED DESCRIPTION

The present disclosure will now be described more fully hereinafter with reference to the accompanying drawings, in which exemplifying embodiments are shown. The present disclosure may, however, be embodied in many different forms and should not be construed as limited to the embodiments set forth herein; rather, these embodiments are provided by way of example so that this disclosure will be thorough and complete, and will fully convey the scope of the present disclosure to those skilled in the art. Like numbers refer to like elements throughout the description.

Figure 1:
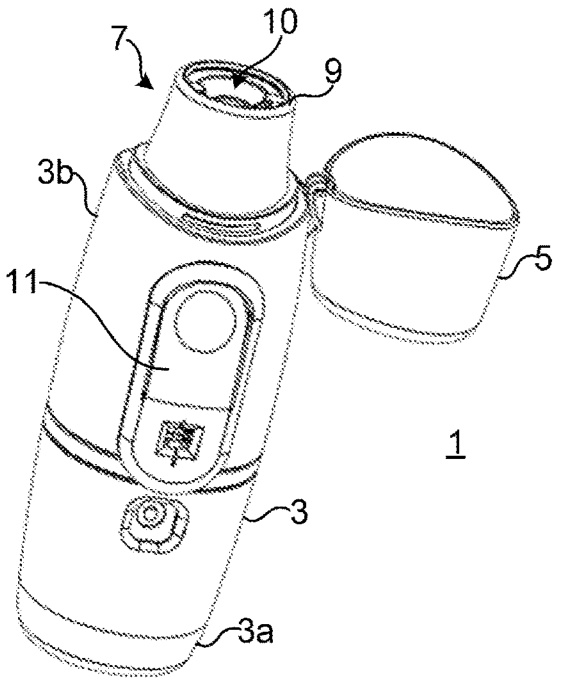
FIG. 1 shows an example of a medicament delivery device comprising an aerosol assembly.

FIG. 1 depicts a perspective view of an example of a medicament delivery device 1. The medicament delivery device 1 is in this example an inhaler but could alternatively for example be an eye dispenser.

The medicament delivery device 1 comprises a housing 3. The housing 3 has a rear portion 3*a* and a front portion 3*b*. The medicament delivery device 3 also comprises a cap 5. In the present example, the cap 5 is hingedly connected to the front portion 3*b* of the housing 3.

The medicament delivery device 1 comprises an aerosol assembly 7. The aerosol assembly 7 forms a front portion of the medicament delivery device 1. The aerosol assembly 7 forms part of an aerosol interface for expulsion of medicament from the medicament delivery device 1 as an aerosol. The medicament delivery device 1 comprises a mouth piece 9. The mouth piece 9 is provided with a central through-opening 10. The central through-opening 10 is in fluid connection with interior of the medicament delivery device 1, specifically with the medicament container contained therein.

The cap 5 can be moved to a closed position in which it covers the aerosol assembly 7. This is normally the case when the medicament delivery device 1 is not in use. In FIG. 1, the cap 5 has been folded to the side to an open position by its hinged connection to expose the mouth piece 9. The cap 5 is set in the open position when the medicament delivery device 1 is to be used.

The mouth piece 9 may be placed against the mouth of the user of the medicament delivery device 1. The medicament delivery device 1 comprises an activation member 11 configured to trigger a medicament delivery. A user can activate the medicament delivery device 1 to achieve a medicament delivery by means of the activation member 11. A medicament is then expelled as an aerosol through the mouth piece 9.

Figure 2:
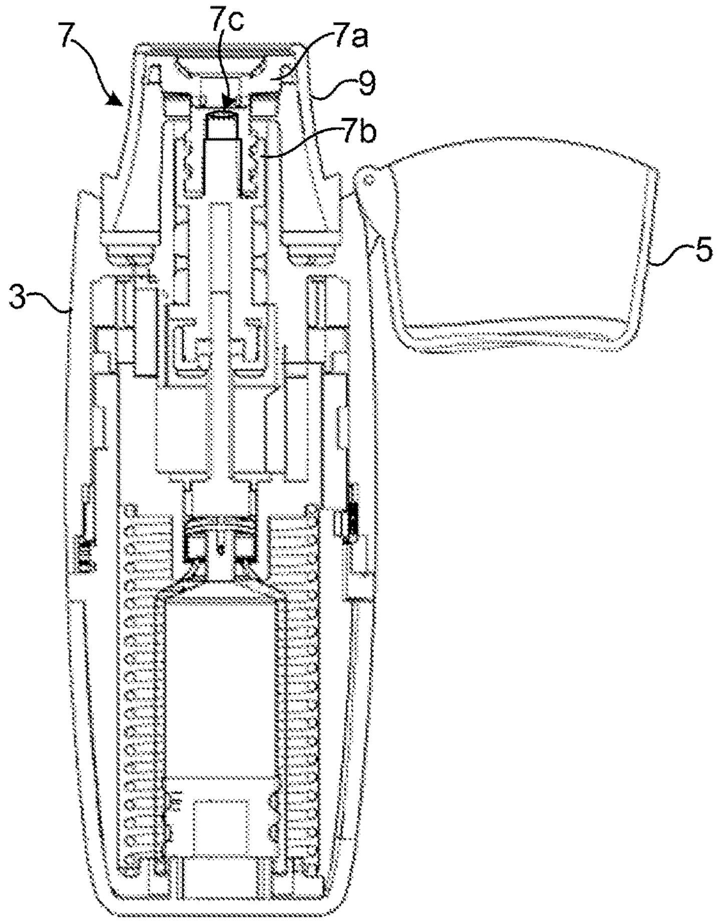
FIG. 2 a longitudinal section of the medicament delivery device in FIG. 1.

FIG. 2 shows a longitudinal section of the medicament delivery device 1. The aerosol assembly 7 comprises a holding structure 7*a* attached to the mouth piece 9. The aerosol assembly 7 comprises a base member 7*b* configured to be connected to the holding structure 7*a*. Further, the aerosol assembly 7 comprises a nozzle assembly 7*c*, including a nozzle chip (not shown in FIG. 2) held by the holding structure 7*a*. The nozzle chip is configured to create an aerosol of medicament flowing through the nozzle chip when medicament administration is being performed. The nozzle chip is arranged such that the aerosol can exit the medicament delivery device 1 through the central through-opening of the mouth piece 9. The base member 7*b* extends into the housing 3 and is configured to fixate the holding structure 7*a* relative to the housing 3. The base member may for example form part of the "power pack" of the medicament delivery device 1, i.e. those components which provide the power for expelling the medicament, or it may be a component separate from the "power pack".

The general operation of the medicament delivery device 1 will not be discussed any further herein as the present disclosure is directed to the aerosol assembly 7, and the general operation of the medicament delivery device 1 would as such be apparent to the skilled person.

Figure 3:
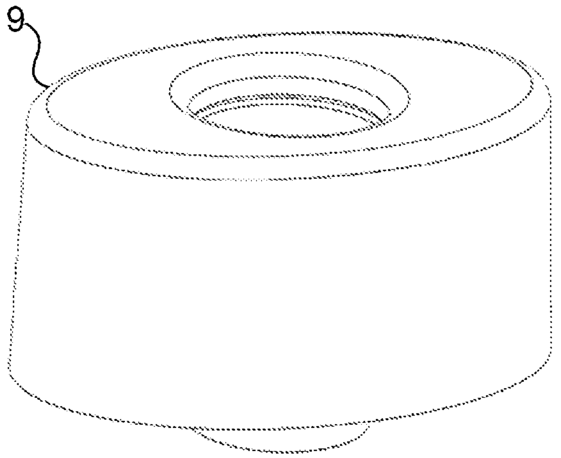
FIG. 3 shows a perspective view of an example of a mouthpiece attached to an aerosol assembly.
Figure 4:
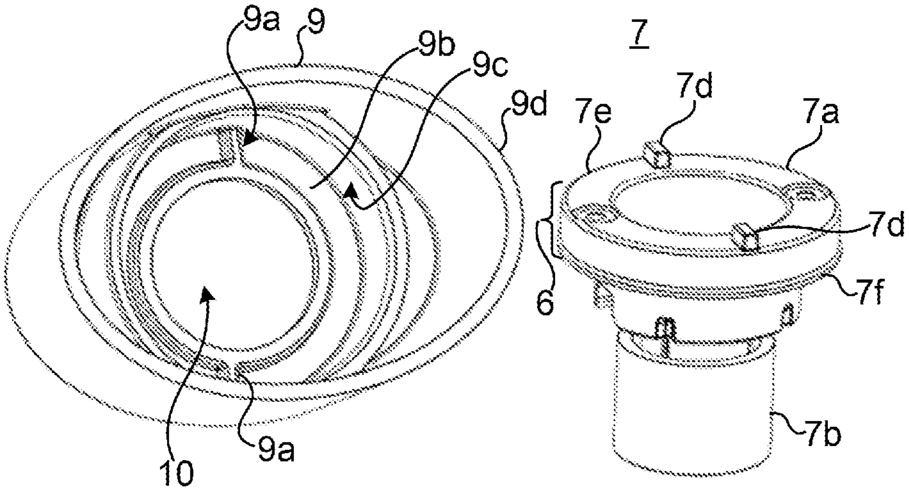
FIG. 4 shows a perspective view of the mouthpiece and the aerosol assembly in FIG. 3.

FIG. 3 depicts the aerosol assembly 7 and the mouth piece 9. FIG. 4 shows a bottom view of the mouth piece 9 to the left and the aerosol assembly 7 to the right.

The mouth piece 9 is configured to receive the holding structure 7*a*. The holding structure 7*a* is arranged concentrically with the mouth piece 9. The mouth piece 9 is configured to be fixedly attached to the housing 3, to an internal component of the medicament delivery device 1 contained in the housing 3, or to the aerosol assembly 7, e.g. to the holding structure or to the base member. The mouth piece 9 is configured to be rotationally fixed relative to the housing 3. For example, the mouth piece 9 may be configured to engage with the housing 3 and/or an internal component of the medicament delivery device 1 by means of a snap-fit structure.

The mouth piece 9 is configured to prevent rotation of the holding structure 7*a* in a mounted state of the medicament delivery device 1. The mouth piece 9 has an inner surface 9*b* provided with first blocking structures 9*a*, which extend axially towards the holding structure 7*a*. The first blocking structures 9*a* may for example be axially extending protrusions or tabs configured to engage with the holding structure 7*a*. The holding structure 7*a* comprises second blocking structures 7*d* configured to cooperate with the first blocking structures 9*a* such that rotation of the holding structure 7*a* may be prevented. The second blocking structures 7*d* may be provided on a top surface 7*e* of the holding structure 7*a*, facing the inner surface 9*b* of the mouth piece 9. The second blocking structures 7*d* may be axially extending protrusions or tabs extending towards the inner surface 9*b* of the mouth piece 9. The second blocking structures 7*d* may for example be arranged at 180 degrees from each other on the top surface 7*e* of the holding structure 7*a*. The first blocking structures 9*a* may be arranged at corresponding locations on the inner surface 9*b* such that they engage with the second blocking structures 7*d*.

The first blocking structures 9*a* and the second blocking structures 7*d* are arranged relative to each other such that the mouth piece 9 can rotate some degrees relative to the holding structure 7*a* during assembly of the medicament delivery device 1 to attain their engaged position.

The holding structure 7*a* is provided with a sealing lip 7*f*. The sealing lip 7*f* extends along the entire perimeter of the holding structure 7*a*. The sealing lip 7*f* is configured to seal the holding structure 7 against the mouth piece 9. The mouth piece 9 comprises an inner wall 9*c* and an outer wall 9*d*. The inner wall 9*c* and the outer wall 9*d* are arranged concentrically. The outer wall 9*d* forms the outer surface of the mouth piece 9. The inner wall 9*c* extends around a top portion 6 of the holding structure 7*a*. According to the present example, the sealing lip 7*f* is configured to bear against the inner surface of the inner wall 9*c* to thereby seal the holding structure 7*a* against the mouth piece 9.

Figure 5:
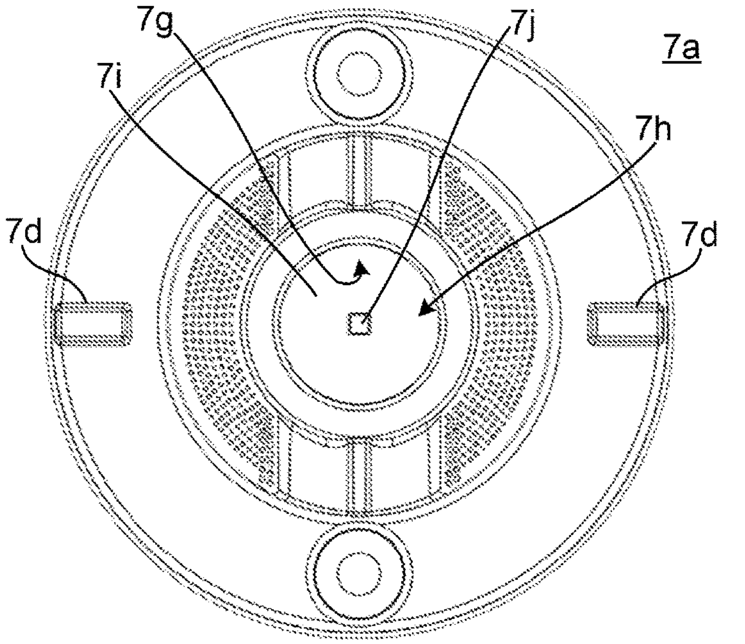
FIG. 5 is a top view of the aerosol assembly in FIG. 3.

FIG. 5 shows a top view of the holding structure 7*a*. The holding structure 7*a* comprises a fluid channel 7*g*. The fluid channel 7*g* extends axially through the holding structure 7*a*. With the term "axial" is meant the central longitudinal axis of the medicament delivery device 1.

The aerosol assembly 7 includes the aforementioned nozzle chip assembly 7*h*. The nozzle chip assembly 7*h* comprises a carrier 7*i* and the nozzle chip 7*j*. The nozzle chip 7*j* is preferably a micro nozzle. The nozzle chip 7*j* is provided on the carrier 7*i*. The nozzle chip 7*j* is attached to the carrier 7*i*. The nozzle chip 7*j* may be bonded to the carrier 7*i*. For example, the nozzle chip 7*j* may be glued to the carrier 7*i*. The carrier 7*i* is a substrate. The carrier 7*i* is attached to the holding structure 7*a*. The carrier 7*i* is arranged fixed relative to the holding structure 7*a*. The carrier 7*i* is arranged in the fluid channel 7*g* such that medicament must flow through the nozzle chip 7*j* to form an aerosol. The nozzle chip 7*j* is hence arranged in the fluid channel 7*g*. The nozzle chip 7*j* may for example be centred in the fluid channel 7*g*, i.e. with respect to the central longitudinal axis of the medicament delivery device 1.

Figure 6:
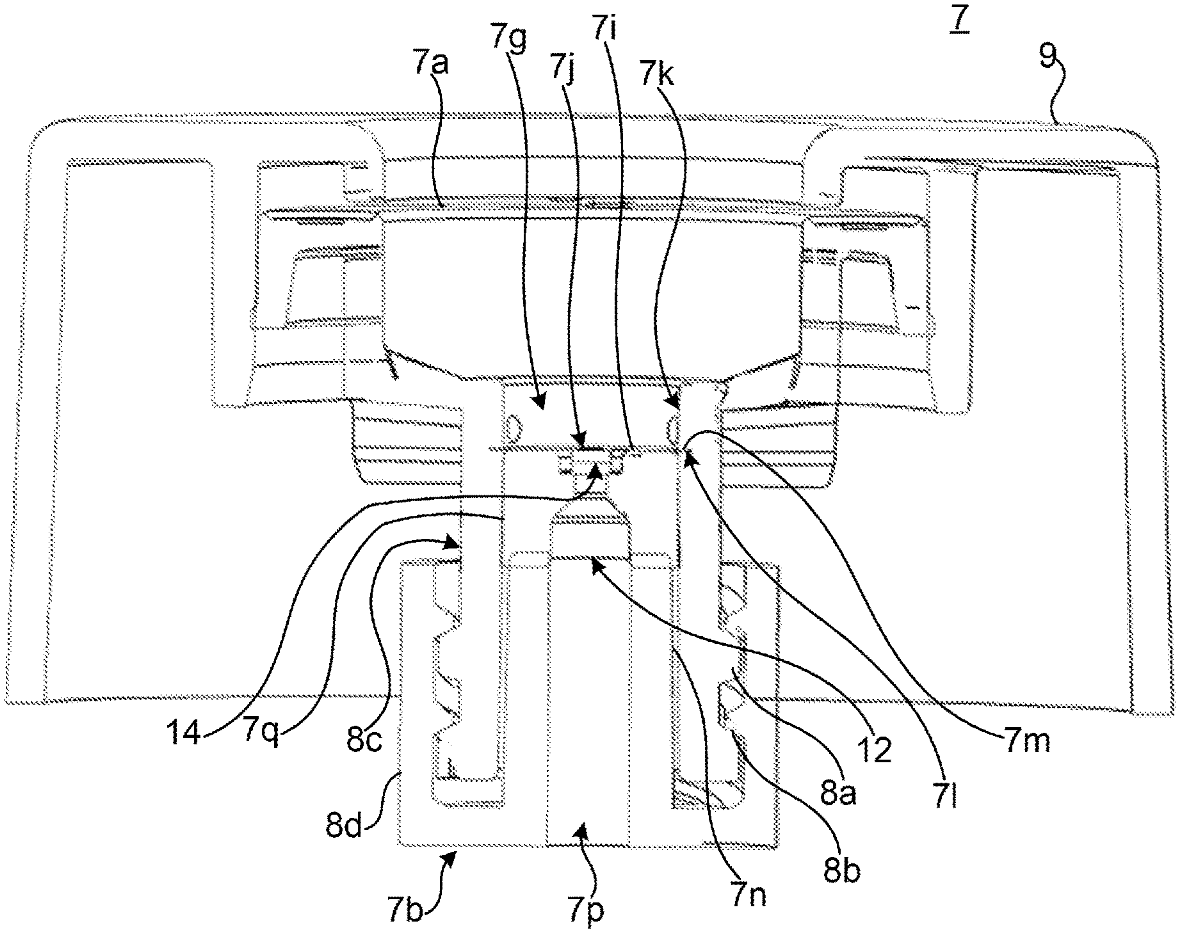
FIG. 6 is a longitudinal section of the aerosol assembly in FIG. 3 with the mouthpiece attached to it.

FIG. 6 depicts a longitudinal section of the aerosol assembly 7. An upper portion of the base member 7*b* is here shown in more detail. The base member 7*b* has a central channel 7*p* connected to the fluid channel 7*g* of the holding structure 7*a*.

The base member 7*b* a is configured to engage with the holding structure 7*a*. The base member 7*b* thereby holds the holding structure 7*a* in place relative to the housing 3. The fluid channel 7*g* extends through the holding structure 7*a*. One end of the fluid channel 7*g* opens into the central through-opening 1*o* of the mouth piece 9.

The fluid channel 7*g* has an inner surface 7*k* provided with an opening 7*l*. The opening 7*l* extends in the circumferential direction along the inner surface 7*k*. The opening 7*l* may be in the form of a slit. The opening 7*l* is configured to receive an outer boundary portion 7*m* of the carrier 7*i*. The carrier 7*i* is thereby fixed to the holding structure 7*a* inside the fluid channel 7*g*.

The base member 7*b* has an axially extending Luer cone 7*n*. The Luer cone 7*n* extends into the fluid channel 7*g* towards the carrier 7*i* and the nozzle chip 7*j*. The Luer cone

*7n* is configured to engage with or bear against the inner surface 7*k* of the fluid channel 7*g*. The Luer cone 7*n* has the central channel 7*p*. The central channel 7*p* extends axially in the Luer cone 7*n*. The central channel 7*p* opens into the fluid channel 7*g* towards the nozzle chip 7*j*. The Luer cone 7*n* does not extend all the way to the carrier 7*i* and the nozzle chip 7*j*.

The aerosol assembly 7 comprises an elastic sealing member 7*q*. The sealing member 7*q* is configured to seal the nozzle chip 7*j* towards the carrier 7*i*. The sealing member 7*q* may be rotationally symmetric. The sealing member 7*q* is made of a viscoelastic material. The viscoelastic material may be an elastomer. The sealing member 7*q* is arranged with a tight fit in the fluid channel 7*g*. The sealing member 7*q* is arranged axially between the Luer cone 7*n* and the carrier 7*i*. The sealing member 7*q* may bear against the Luer cone 7*n* and the carrier 7*i*.

The sealing member 7*q* is provided with a central through-opening 12 arranged coaxially with the central channel 7*p* of the Luer cone 7*n* and the fluid channel 7*g* of the holding structure 7*a*. In the present example, the central through-opening 12 has a varying diameter in the axial direction of the sealing member 7*q*. The diameter of the central through-opening 12 tapers in a direction towards the carrier 7*i*. The diameter of the central through-opening 12 is the same or essentially the same as the diameter of the central channel 7*p* as the central channel 7*p* transitions into the central through-opening 12. The diameter of the central through-opening 12 then tapers and obtains a first constant diameter. The diameter then widens in a direction towards the carrier 7*i*, for example in a discrete step to a second constant or essentially constant diameter forming a nozzle chip cavity 14. The nozzle chip 7*j* is arranged in the central through-opening 12. In the example in FIG. 6 the nozzle chip 7*j* is arranged in the central through-opening 12 where the central through-opening 12 has attained the second diameter, i.e. in the nozzle chip cavity 14.

The holding structure 7*a* is provided with first Luer threads 8*a*. The base member 7*b* is provided with second Luer threads 8*b*. The first Luer threads 8*a* are configured to engage with the second Luer threads 8*b*. The first Luer threads 8*a*, the second Luer threads 8*b* and the Luer cone 7*n* form a Luer lock connection between the holding structure 7*a* and the base member 7*b*.

The holding structure 7*a* has a hollow generally cylindrical end portion 8*c*. The cylindrical end portion 8*c* is provided with the first Luer threads 8*a*. In particular, the cylindrical end portion 8*c* has an external surface provided with the first Luer threads 8*c*. The Luer cone 7*n* is configured to be received into the fluid channel 7*g* in the cylindrical end portion 8*c*. The Luer cone 7*n* extends towards the carrier 7*i*. The base member has an outer wall 8*d* arranged radially outside of and concentrically with the Luer cone 7*n*. The outer wall 8*d* is provided with the second Luer threads 8*b* on its inner surface which faces the Luer cone 7*n*. A portion of the cylindrical end portion 8*c* provided with the first Luer threads 8*a* is arranged concentrically between the outer wall 8*d* and the Luer cone 7*n*. The first Luer threads 8*a* thereby engage with the second Luer threads 8*b*.

Figure 7:
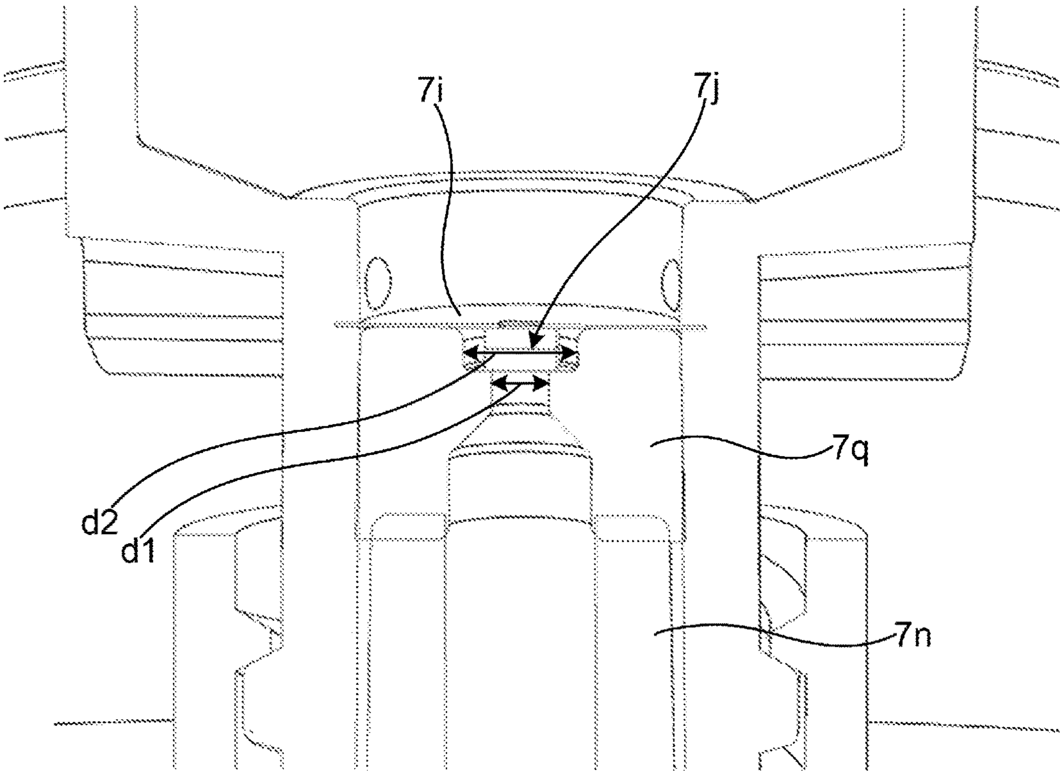
FIG. 7 is a close-up view of the aerosol assembly in FIG. 6.

FIG. 7 shows a close-up view of the region around the nozzle chip 7*j*. It can here better be seen how the diameter of the central through-opening 12 varies in an axial direction towards the carrier 7*i*. In the depicted example, the first constant diameter of the central through-opening 12 is smaller than the corresponding dimensions of the nozzle chip 7*j*. All the liquid flowing through the central through-opening 12 towards the nozzle chip 7*j* will thereby pass through the nozzle chip 7*j*. The nozzle chip 7*j* may be sandwiched between the heel formed due to the step between the first diameter d1 and the second diameter d2 and the carrier 7*i*.

Figure 8:
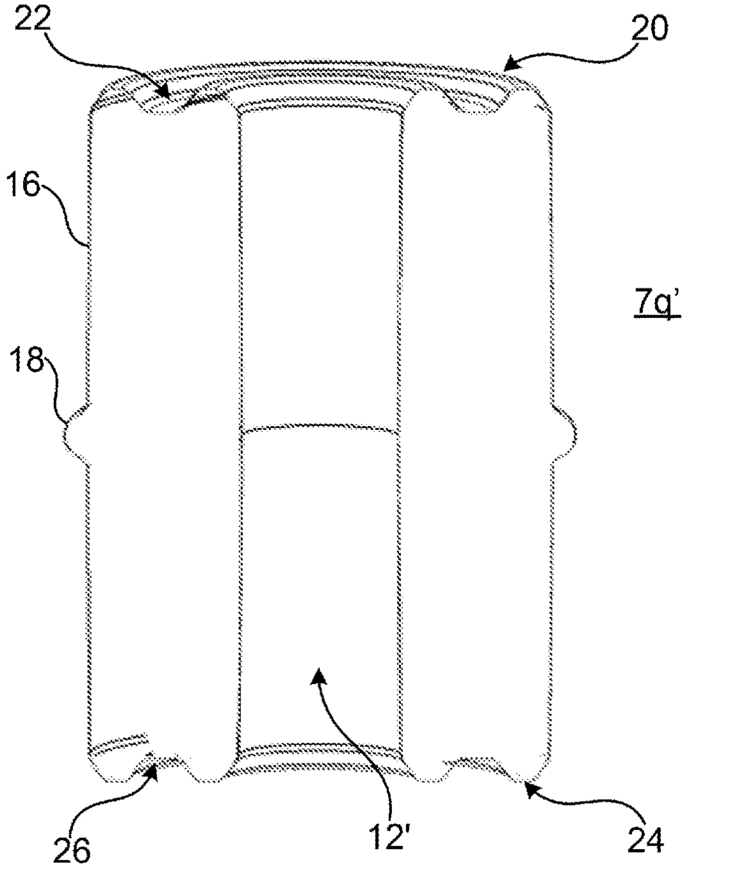
FIG. 8 is an example of an elastic sealing member.

FIG. 8 shows another example of a sealing member 7*q*'. The sealing member 7*q*' has a central through-opening 12' that has a constant diameter along the entire length of the sealing member 7*q*'. The sealing member 7*q*' has an external surface 16 provided with a rib 18 extending in the circumferential direction of the sealing member 7*q*'. The rib 18 may extend along the entire circumference of the sealing member 7*q*'. The rib 18 may for example be arranged axially at or essentially at the mid-point between the two axial ends of the sealing member 7*q*'.

The sealing member 7*q*' has a first end surface 20 which bears against the carrier 7*i*. The first end surface 20 forms a first axial end of the sealing member 7*q*'. The first end surface 20 is provided with a first groove 22 which extends in the circumferential direction around the central through-opening 12'.

The sealing member 7*q*' has a second end surface 24 which bears against an end face of the Luer cone 7*n*. The second end surface 24 forms a second axial end of the sealing member 7*q*', opposite to the first axial end. The second end surface 24 is provided with a second groove 26 which extends in the circumferential direction around the central through-opening 12'.

Figure 9:
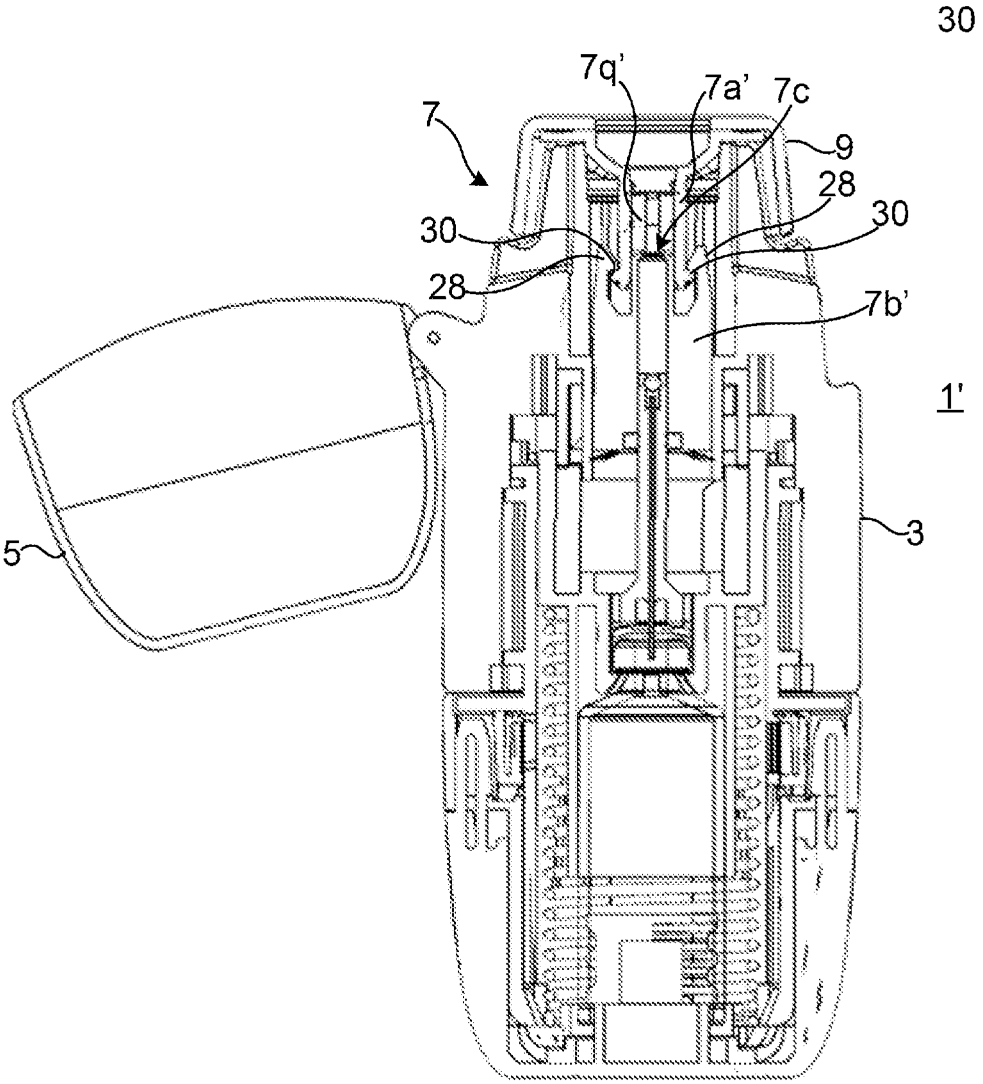
FIG. 9 shows a longitudinal section of another example of a medicament delivery device.

FIG. 9 shows another example of a medicament delivery device 1'. In this example, the base member 7*b*' and the holding structure 7*a*' are configured to interlock with each other by means of a snap-fit mechanism.

The base member 7*a*' is provided with a plurality of gripping arms 28 and the holding structure 7*a*' is provided with radial protrusions 30. Each gripping arm 28 is configured to engage with a respective radial protrusion 30. The gripping arms 28 and the radial protrusions 30 form the snap-fit mechanism.

The radial protrusions 30 extend radially from the outer surface of the cylindrical end portion of the holding structure 7*a*'. The base member 7*b*' has a cylindrical base member end portion configured to be received by the fluid channel of the holding structure 7*a*'. The sealing member 7*q* or 7*q*' is configured to be arranged between the carrier and the end face of the cylindrical base member end portion.

The present disclosure has mainly been described above with reference to a few examples. However, as is readily appreciated by a person skilled in the art, other embodiments than the ones disclosed above are equally possible within the scope of the present disclosure, as defined by the appended claims.

The invention claimed is:

1. An aerosol assembly for a medicament delivery device, the aerosol assembly comprising:

a nozzle chip assembly including a carrier and a nozzle chip provided on the carrier, a holding structure having a fluid channel extending through the holding structure, wherein the nozzle chip assembly is configured to be mounted into the fluid channel such that fluid flowing through the fluid channel passes through the nozzle chip, an elastic sealing member configured to be arranged with a tight fit in the fluid channel, the sealing member having a central through-opening configured to receive the nozzle chip to seal the nozzle chip towards the carrier, and a base member having a Luer cone configured to extend into the fluid channel towards the nozzle chip assembly, the Luer cone having a central channel extending through the base member and configured to extend coaxially with the fluid channel, wherein the base member and the holding structure have Luer threads by which the base member and the holding structure are configured to be connected, wherein the central through-opening of the sealing member is configured to open towards the central channel, wherein the sealing member is configured to be arranged axially between the Luer cone and the carrier, and wherein the sealing member is configured to be in contact with the Luer cone and with the carrier.

2. The aerosol assembly as claimed in claim 1, wherein the fluid channel has an inner surface provided with a circumferentially extending opening, wherein the carrier has an outer boundary portion mounted into the opening to hold the carrier in place.

3. The aerosol assembly as claimed in claim 1, wherein the sealing member comprises a viscoelastic material.

4. The aerosol assembly as claimed in claim 3, wherein the viscoelastic material is an elastomer.

5. The aerosol assembly as claimed in claim 1, wherein the sealing member is rotationally symmetric.

6. The aerosol assembly as claimed in claim 1, wherein the central through-opening (12') has a constant inner diameter along its entire extension.

7. The aerosol assembly as claimed in claim 1, wherein the sealing member is configured to be mounted in the fluid channel with a mounting compression of between 0.2 to 0.6 mm.

8. The aerosol assembly as claimed in claim 1, wherein the sealing member has an external surface provided with a rib extending in a circumferential direction of the sealing member.

9. The aerosol assembly as claimed in claim 1, wherein the holding structure has a hollow generally cylindrical end portion in which the fluid channel extends axially, wherein the cylindrical end portion has an external surface provided with first Luer threads, and wherein the base member has an outer wall arranged concentrically with the Luer cone, wherein the cylindrical end portion is configured to be arranged concentrically between the Luer cone and the outer wall, the outer wall having second Luer threads configured to engage with the first Luer threads.

10. A medicament delivery device comprising an aerosol assembly as claimed in claim 1.

11. The medicament delivery device as claimed in claim 10, wherein the medicament delivery device is an inhaler.

12. An aerosol assembly for an inhaler, where the aerosol assembly comprises:

a nozzle chip assembly including a carrier and a nozzle chip provided on the carrier;

a holding structure having a fluid channel extending through the holding structure, where the nozzle chip assembly is configured to be mounted into the fluid channel such that fluid flowing through the fluid channel passes through the nozzle chip;

an elastic and rotationally symmetric sealing member is arranged with a tight fit in the fluid channel, where the sealing member has a central through-opening configured to receive the nozzle chip; and a base member having a Luer cone configured to extend into the fluid channel towards the nozzle chip assembly, the Luer cone having a central channel extending through the base member and configured to extend coaxially with the fluid channel, wherein the base member and the holding structure have Luer threads by which the base member and the holding structure are configured to be connected, wherein the central through-opening of the sealing member is configured to open towards the central channel, wherein the sealing member is configured to be arranged axially between the Luer cone and the carrier, and wherein the sealing member is configured to be in contact with the Luer cone and with the carrier.

* * * * *